US012654019B2

(12) United States Patent (10) Patent No.: US 12,654,019 B2
Badie et al. (45) **Date of Patent: *Jun. 16, 2026**

(54) METHOD AND SYSTEM UTILIZING A DEVICE-BASED ATRIO-VENTRICULAR DELAY ADJUSTMENT

(71) Applicant: Pacesetter, Inc, Sylmar, CA (US)

(72) Inventors: Nima Badie, Berkeley, CA (US); Jan O. Mangual-Soto, Rho (IT); Luke C. McSpadden, Los Angeles, CA (US); Aditya Goil, Stevenson Ranch, CA (US); Kyungmoo Ryu, Palmdale, CA (US)

(73) Assignee: Pacesetter, Inc., Sylmar (CA)

( * ) Notice: Subject to any disclaimer, the term of this patent is extended or adjusted under 35 U.S.C. 154(b) by 248 days.

This patent is subject to a terminal disclaimer.

(21) Appl. No.: 18/503,287

(22) Filed: Nov. 7, 2023

(65) Prior Publication Data

US 2024/0066307 A1 Feb. 29, 2024

Related U.S. Application Data

(63) Continuation of application No. 17/449,231, filed on Sep. 28, 2021, now Pat. No. 11,844,950, which is a
(Continued)

(51) Int. Cl.
*A61N 1/365* (2006.01)
*A61N 1/362* (2006.01)
(Continued)

(52) U.S. Cl.
CPC ....... *A61N 1/3682* (2013.01); *A61N 1/36592* (2013.01)

(58) Field of Classification Search
CPC .............. A61N 1/3682; A61N 1/36592; A61N 1/3706; A61N 1/3627
See application file for complete search history.

(56) References Cited

U.S. PATENT DOCUMENTS

| 7,643,878 B1 | 1/2010 | Muller et al. |
| 2004/0147966 A1 | 7/2004 | Ding et al. |

(Continued)

OTHER PUBLICATIONS

Badie et al. "Programming Cardiac Resynchronization Therapy for Electrical Synchrony: Reaching Beyond Left Bundle Branch Block and Left Ventricular Activation Delay" Journal of American Heart Association; 2018 (13 pages).

(Continued)

*Primary Examiner* — Brian T Gedeon

(74) *Attorney, Agent, or Firm* — Dean D. Small; Carroll, Hoette & Butscher, LLC

(57) ABSTRACT

A method and device for dynamic device based AV delay adjustment are provided. The method provides electrodes that are configured to be located proximate to an atrial (A) site and a right ventricular (RV) site. The method utilizes one or more processors, in an implantable medical device (IMD), for detecting an atrial paced (Ap) event or atrial sensed (As) event. The method determines a measured AV interval corresponding to an interval between the Ap event or the As event and a ventricular sensed event and calculates a percentage-based (PB) offset based on the measured AV interval. The method automatically dynamically adjusting an AV delay, utilized by the IMD, based on the measured AV interval and the PB offset and manages a pacing therapy, utilized by the IMD, based on the AV delay after the adjusting operation.

18 Claims, 5 Drawing Sheets

Related U.S. Application Data continuation of application No. 16/574,959, filed on Sep. 18, 2019, now Pat. No. 11,154,719.

(60) Provisional application No. 62/734,830, filed on Sep. 21, 2018.

(51) Int. Cl.
    *A61N 1/368*         (2006.01)
    *A61N 1/37*          (2006.01)

(56)             References Cited

U.S. PATENT DOCUMENTS

| | | | |
|---|---|---|---|
| 2008/0140147 A1 | 6/2008 | Husby | |
| 2009/0234414 A1 | 9/2009 | Sambelashvili et al. | |
| 2009/0281591 A1 | 11/2009 | Shuros et al. | |
| 2017/0246460 A1 | 8/2017 | Ghosh | |
| 2020/0094056 A1* | 3/2020 | Badie ..................... | A61B 5/287 |
| 2022/0080209 A1* | 3/2022 | Mangual-Soto ..... | A61N 1/3682 |

OTHER PUBLICATIONS

International Search Report and Written Opinion for corresponding Application No. PCT/US20199/051949 dated Dec. 11, 2019 (16 pages).
Office Action for corresponding CN Application No. 201980061726.7 dated Nov. 18, 2024 (23 pages).

* cited by examiner

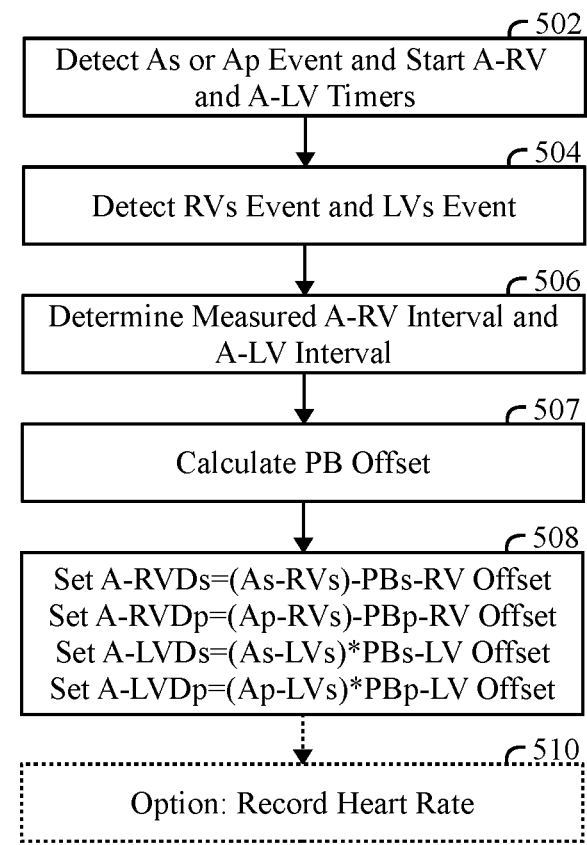

Detect As or Ap Event and Start A-RV
and A-LV Timers ⌐502

Detect RVs Event and LVs Event ⌐504

Determine Measured A-RV Interval and
A-LV Interval ⌐506

Calculate PB Offset ⌐507

Set A-RVDs=(As-RVs)-PBs-RV Offset
Set A-RVDp=(Ap-RVs)-PBp-RV Offset
Set A-LVDs=(As-LVs)*PBs-LV Offset
Set A-LVDp=(Ap-LVs)*PBp-LV Offset ⌐508

Option: Record Heart Rate ⌐510

Figure 5

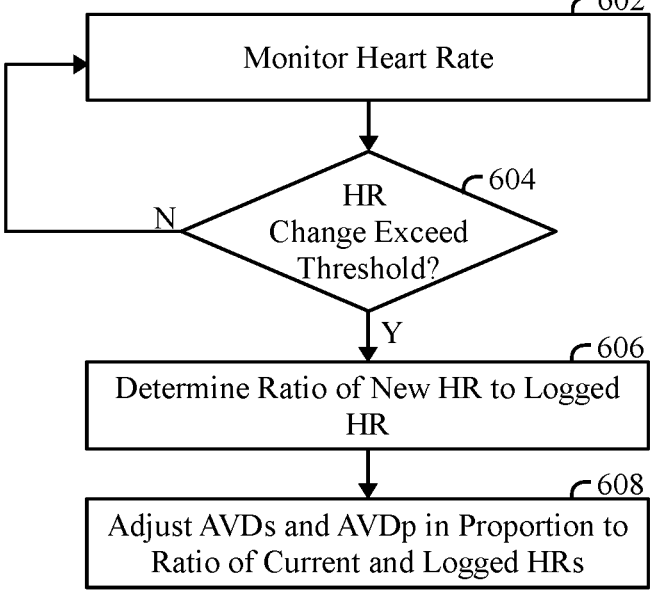

Monitor Heart Rate ⌐602

HR
Change Exceed
Threshold? ⌐604

Determine Ratio of New HR to Logged
HR ⌐606

Adjust AVDs and AVDp in Proportion to
Ratio of Current and Logged HRs ⌐608

Figure 6

METHOD AND SYSTEM UTILIZING A DEVICE-BASED ATRIO-VENTRICULAR DELAY ADJUSTMENT

RELATED APPLICATION

This application is a continuation of U.S. application Ser. No. 17/449,231, filed 28 Sep. 2021, which is a continuation of U.S. application Ser. No. 16/574,959, filed 18 Sep. 2019 (now U.S. Pat. No. 11,154,719, issued 26 Oct. 2021), which claims priority to U.S. Application No. 62/734,830, filed 21 Sep. 2018; the entire disclosures of which are incorporated by reference herein.

FIELD OF THE INVENTION

Embodiments herein generally relate to implantable medical devices, and more particularly to adjusting atrioventricular delay based on a percentage based offset derived from measured AV interval.

BACKGROUND OF THE INVENTION

Advances in implantable medical devices (IMD) and left ventricular (LV) lead design has improved electrical stimulation, delays, and pacing, resulting in a better patient outcome. Loss of atrioventricular (AV) electrical and mechanical synchrony can result in inadequate ventricular depolarization, leading to suboptimal therapy. Optimal AV delay (AVD) can improve electrical synchrony by fusing an intrinsic conduction wavefront and device pacing to produce an enhanced depolarization of the ventricles and increased cardiac output.

Cardiac resynchronization therapy (CRT) has been shown to improve hemodynamics in heart failure (HF) patients, particularly when the AVD has been individualized for each patient. AVD programming for each patient is commonly performed in-clinic at implant, when an AVD is selected for each patient based on echocardiographic, ECG, or blood pressure metrics. This one-time, static AVD selection does not account for short-term changes (hourly; e.g., exercise, sleep) or long-term changes (monthly; e.g., disease progression) in a patient's electromechanical conduction after the patient leaves the clinic.

At least one approach has been proposed that adjusts the AVD over time. In this conventional approach, an AV interval (AVI) is measured and the AVD is set to equal the AV interval reduced by a fixed amount that the clinician programs. Unfortunately, this conventional algorithm has two drawbacks. First, the method of the AVD value simply subtracts a static value (e.g., 50 ms). However, the cardiac conduction velocity, and thus the intrinsic AV conduction interval, is heart rate dependent. Faster heart rates are typically associated with shorter AV conduction intervals.

The second drawback of the conventional algorithm is that the interventricular (i.e., RV-LV) timing is not adequately addressed. While most users opt for the default "near-simultaneous" RV-LV biventricular pacing, providing simultaneous RV-LV biventricular pacing does not customize A-RV and A-LV timing independently.

A need remains for methods and systems that provide dynamic AV timing adjustment that adapts to each patient's continually changing cardiovascular status.

SUMMARY

In accordance with embodiments herein, a method for dynamic device based AV delay adjustment is provided. The method provides electrodes that are configured to be located proximate to an atrial (A) site and a right ventricular (RV) site. The method utilizes one or more processors, in an implantable medical device (IMD), for detecting an atrial paced (Ap) event or atrial sensed (As) event. The method determines a measured AV interval corresponding to an interval between the Ap event or the As event and a ventricular sensed event and calculates a percentage-based (PB) offset based on the measured AV interval. The method automatically dynamically adjusting an AV delay, utilized by the IMD, based on the measured AV interval and the PB offset and manages a pacing therapy, utilized by the IMD, based on the AV delay after the adjusting operation.

Optionally, the calculating operation may further comprise setting the PB offset to equal a programmed percentage of the measured AV interval. The adjusting operation may further comprise setting the AV delay to correspond to a difference between the measured AV interval and the PB offset. The calculating and adjusting operations may further comprise setting the AV delay, in connection with the As event, as $AVDs=[(As\text{-}Vs\ interval)-(PB\ offset)]$, wherein the PB offset$=(As\text{-}Vs\ interval)*P1\%]$, the As-Vs interval may correspond to the measured AV interval between the As event and a sensed ventricular (Vs) event, and the P1% may correspond to a pre-programmed percentage.

Optionally, the method may provide an electrode that may be configured to be proximate to a left ventricular (LV) site. The measured AV interval may comprise a measured A-RV interval and a measured A-LV interval. The adjusting operation may further comprise adjusting, as the AV delay a delay that may be associated with the As event to a right sensed ventricular (RVs) event as $A\text{-}RVDs=[(As\text{-}RVs\ interval)-(PBs\text{-}RV\ offset)]$, wherein the PBs-RV offset may represent a first percentage based offset between the As event and the RVs event and a delay that may be associated with the As event to a left ventricular sensed (LVs) event as $A\text{-}RVDs=[(As\text{-}LVs\ interval)-(PBs\text{-}LV\ offset)]$, wherein PBs-LV offset may represent a second percentage based offset between the As event and the LVs event.

Optionally, the method may comprise logging a base heart rate associated with the measured AV interval. The method may monitor a current heart rate, and may automatically repeat the determining, calculating and adjusting operations when the current heart rate changes by more than a predetermined threshold relative to the base heart rate. The method may extend the AV delay in proportion to a ratio between the current heart rate and the base heart rate when the current heart rate is slower than the base heart rate. The method may extend the AV delay to correspond to a default search AV delay ($AVD_{search}$). The method may sensing cardiac activity for a predetermined number of cardiac beats, may identifying whether the cardiac activity is indicative of a conduction block condition or non-conduction block condition and may repeat the determining, calculating and adjusting operations only when the non-conduction block condition is identified.

Optionally, the identifying operation may comprise identifying the cardiac activity to be indicative of a conduction block condition when fewer than a select number of cardiac beats exhibit sensed ventricular events during the default search AV delay $AVD_{search}$. The adjusting may comprise adjusting a sensed AV delay (AVDs) and a paced AV delay (AVDp). The method may further comprise identifying a presence of conduction block and, in response thereto, revert the AVDs and base AVDp to AVDs-base and AVDp-base programmed lengths, respectively. The method may maintain the base AVDp-base and AVDs-base programmed lengths for a select second number of cardiac beats.

In accordance with embodiments herein, an implantable medical device (IMD) is provided. The device comprises electrodes that are configured to be located proximate to an atrial (A) site and a right ventricular (RV) site. Memory stores program instructions. One or more processors are configured to implement the program instructions to detect an atrial paced (Ap) event or atrial sensed (As) event, determine a measured AV interval corresponding to an interval between the Ap event or the As event and a ventricular sensed event and calculate a percentage-based (PB) offset based on the measured AV interval. The device automatically dynamically adjust an AV delay, utilized by the IMD, based on the measured AV interval and the PB offset and manages a pacing therapy, utilized by the IMD, based on the AV delay after the adjusting operation.

Optionally, the one or more processors may be configured to set the PB offset to equal a programmed percentage of the measured AV interval, and may set the AV delay to correspond to a difference between the measured AV interval and the PB offset. The one or more processors may be configured to perform the calculating and adjusting operations by setting the AV delay, in connection with the As event, as AVDs=[(As-Vs interval)–(PB offset)], wherein the PB offset=(As-Vs interval)*P1%], the As-Vs interval may correspond to the measured AV interval between the As event and a sensed ventricular (Vs) event, and the P1% may correspond to a pre-programmed percentage.

The device may comprise an electrode that may be configured to be proximate to a left ventricular (LV) site. The measured AV interval may comprise a measured A-RV interval and a measured A-LV interval. The one or more processors may adjust the AV delay by adjusting, as the AV delay: a delay associated with the As event to a right sensed ventricular (RVs) event as A-RVDs=[(As-RVs interval)–(PBs-RV offset)], wherein the PBs-RV offset may represent a first percentage based offset between the As event and the RVs event and a delay associated with the As event to a left ventricular sensed (LVs) event as A-RVDs=[(As-LVs interval)–(PBs-LV offset)], wherein PBs-LV offset may represent a second percentage based offset between the As event and the LVs event.

Optionally, the one or more processors may be configured to log a base heart rate associated with the measured AV interval. The one or more processors may be configured to monitor a current heart rate, and may automatically repeat the determining, calculating and adjusting operations when the current heart rate changes by more than a predetermined threshold relative to the base heart rate. The one or more processors may be configured to extend the AV delay in proportion to a ratio between the current heart rate and the base heart rate when the current heart rate is slower than the base heart rate. The one or more processors may be configured to: extend the AV delay to correspond to a default search AV delay (AVD$_{search}$), may sense cardiac activity for a predetermined number of cardiac beats, may identify whether the cardiac activity is indicative of a conduction block condition or non-conduction block condition and may repeat the determining, calculating and adjusting operations only when the non-conduction block condition is identified.

Optionally, the one or more processors may be configured to perform the identifying operation by identifying the cardiac activity to be indicative of a conduction block condition when fewer than a select number of cardiac beats exhibit sensed ventricular events during the default search AV delay AVD$_{search}$. The one or more processors may be configured to adjust a sensed AV delay (AVDs) and a paced AV delay (AVDp), may identify a presence of conduction block and, in response thereto, revert the AVDs and base AVDp to AVDs-base and AVDp-base programmed lengths, respectively and may maintain the base AVDp-base and AVDs-base programmed lengths for a select second number of cardiac beats.

BRIEF DESCRIPTION OF THE DRAWINGS

FIG. 5 illustrates a process for dynamically adjusting paced and sensed AV delays in accordance with embodiments herein.

FIG. 6 illustrates a process for automatically adjusting sensed and paced AV delays, in connection with changes in heart rate, in accordance with embodiments herein.

DETAILED DESCRIPTION

Figure 1:
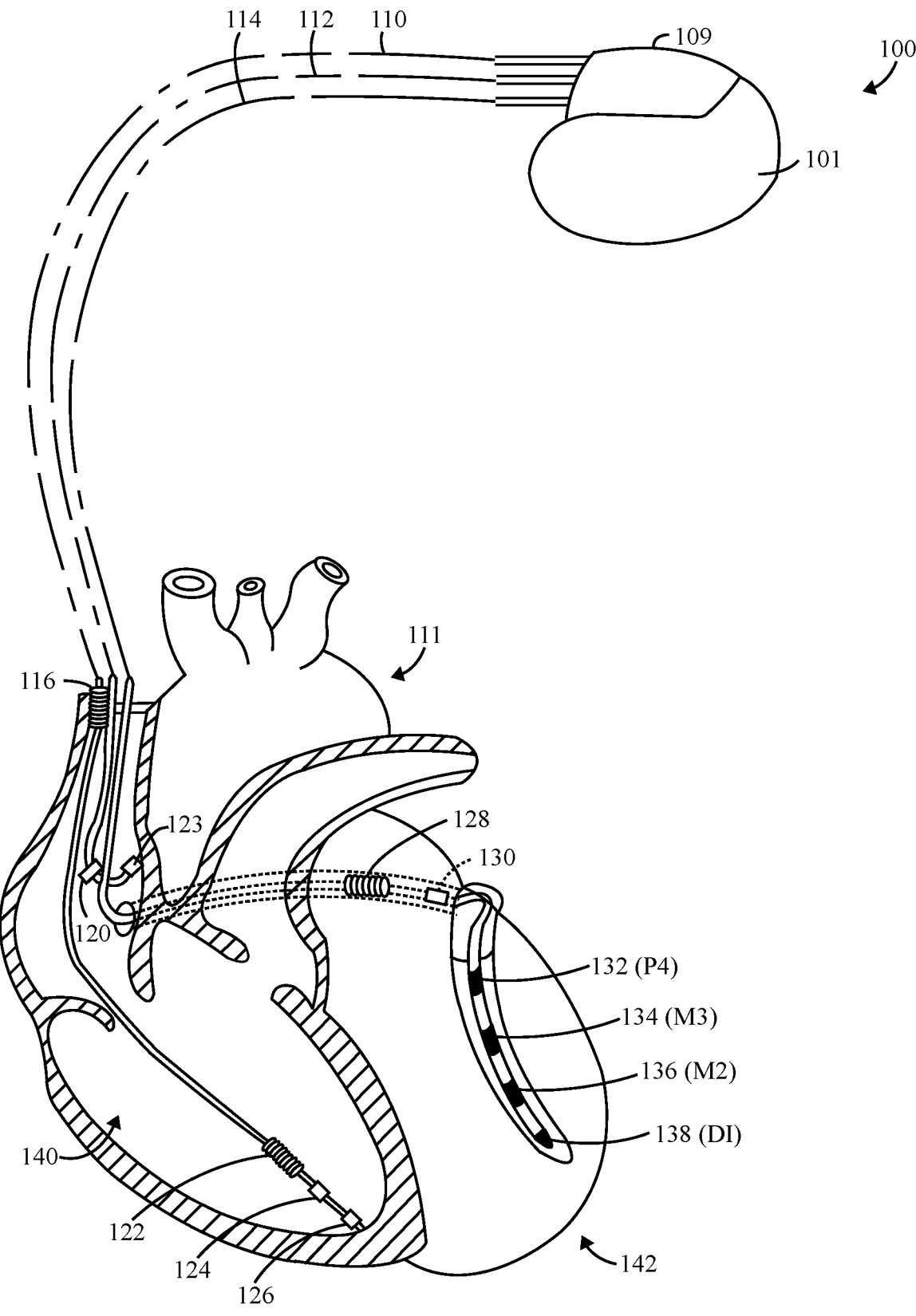
FIG. 1 illustrates an implantable medical device (IMD) intended for subcutaneous implantation at a site near the heart in accordance with embodiments herein.

The term "As-Vs interval", as used herein, refers to a measured intrinsic conduction time from a sensed atrial (As) event to a sensed ventricular (Vs) event. The sensed ventricular event may be a right ventricular event or a left ventricular event. The term "Ap-Vs interval", as used herein, refers to a measured intrinsic conduction time from a paced atrial (Ap) event to a sensed ventricular (Vs) event. The sensed ventricular event may be a right ventricular event or a left ventricular event.

The term "As-RVs interval", as used herein, refers to a measured intrinsic conduction time from a sensed atrial (As) event to a sensed right ventricular (RVs) event. The term "Ap-RVs interval", as used herein, refers to a measured intrinsic conduction time from a paced atrial (Ap) event to a sensed right ventricular (RVs) event.

The term "As-LVs interval", as used herein, refers to a measured intrinsic conduction time from a sensed atrial (As) event to a sensed left ventricular (LVs) event. The term "Ap-LVs interval", as used herein, refers to a measured intrinsic conduction time from a paced atrial (Ap) event to a sensed left ventricular (LVs) event.

The term "PBs-RV offset" refers to a percentage-based (PB) offset calculated based on a measured As-RVs interval.

The term "PBp-RV offset" refers to a percentage-based offset calculated based on a measured Ap-RVs interval.

The term "PBs-LV offset" refers to a percentage-based offset calculated based on a measured As-LVs interval.

The term "PBp-RV offset" refers to a percentage-based offset calculated based on a measured Ap-LVs interval.

The terms "atrioventricular delay" and "AVD" refer to a programmed time delay to be used by the implantable medical device in connection with delivering therapy.

The term "AVDs" refer to an AVD in connection with delivering therapy at a ventricular site following a sensed atrial event, when an intrinsic ventricular event does not occur before AVD expires.

The term "AVDp" is used to refer to an AVD in connection with delivering therapy at a ventricular site following a paced atrial event, when an intrinsic ventricular event does not occur before AVD expires.

The term "LV only pacing" refers to a mode of operation for an implanted medical device in which the LV is paced but the RV is not paced.

In accordance with embodiments herein, methods and systems are described for dynamic adjustment of AVD while accounting for a dependence of the intrinsic AV conduction interval on heart rate. Embodiments herein calculate an offset as a percentage of a real-time measured AV interval, and dynamically adjust the AVD by subtracting the percentage offset from the measured AV interval. Additionally or alternatively, embodiments may apply a percent-based offset to the RV and LV leads independently, based on the respective AV interval measurements. Thus, biventricular pacing may be delivered in terms of two AVD values (A-RV delay and A-LV delay), rather than based on one AVD and a programmed interventricular delay (VVD), which traditionally determines the timing of LV-pacing relative to RV-pacing.

Embodiments herein subtract a dynamic PB offset from the measured AV interval, where the dynamic PB offset is a programmed percentage of the measured AV interval (e.g., 20%). By dynamically programming the AVD to the intrinsic AV interval reduced by a percentage of the intrinsic AV interval, embodiments herein maintain fusion between (a) the intrinsic wavefront conducting down the septum and (b) the RV- and LV-paced beats, over a broad range of heart rates. Further, embodiments herein achieve a "triple-fusion" of all 3 wavefronts (e.g., intrinsic A-V conduction, RV-paced beat, and LV-paced beat). In addition, embodiments herein afford the ability to independently program A-RV and A-LV delays in the same manner. In other words, the A-RV and A-LV delays may each have a separate offset that is determined relative to the A-RVs and A-LVs intervals, respectively (e.g., 20% of A-RV interval and 40% of A-LV interval). The new AVD values are programmed to be shorter than the measured AV interval's in connection with paced and/or sensed atrial events. The percentage offset may be programmable to allow for patient-specific optimization (e.g., 5-50% in increments of 5%, with a default value of 20%).

In accordance with embodiments herein, the percent-based offsets can be expanded to apply independently to the RV and LV leads, based on the respective AV interval measurements. Specifically, the As-RVs interval (during A-sensing) or the Ap-RVs interval (during A-pacing) are measured, and the A-RV delay is dynamically programmed by subtracting a percentage of the Ap-RVs or As-RVs interval (e.g., 20%), while a parallel programming of the A-LV delay occurs in the same manner. In general, the PB offset used for the A-LV delay should be larger (e.g., 40%) than for the A-RV delay, as the LV-paced wavefront must travel further to simultaneously collide with the intrinsic AV conduction and RV-paced wavefront. These two independent AVD values may be calculated based on the respective AV intervals corresponding to the two pacing vectors used (e.g., A-RV and A-LVD1), both of which can be measured during the same cardiac beat.

FIG. 1 illustrates an implantable medical device (IMD) 100 intended for subcutaneous implantation at a site near the heart 111, in accordance with embodiments herein. The IMD 100 may be a dual-chamber stimulation device, capable of treating both fast and slow arrhythmias with stimulation therapy, including cardioversion, pacing stimulation, an implantable cardioverter defibrillator, suspend tachycardia detection, tachyarrhythmia therapy, and/or the like. The IMD 100 may include a housing 101 to hold the electronic/computing components. The housing 101 (which is often referred to as the "can," "case," "encasing," or "case electrode") may be programmably selected to act as the return electrode for certain stimulus modes. The housing 101 further includes a connector 109 with a plurality of terminals 200-210 (shown in FIG. 2).

The IMD 100 is shown in electrical connection with a heart 111 by way of a left atrial (LA) lead 120 having a right lead 112 and a left atrial (LA) ring electrode 128. The IMD 100 is also in electrical connection with the heart 111 by way of a right ventricular (RV) lead 110 having, in this embodiment, a left ventricle (LV) electrode 132 (e.g., P4), an LV electrode 134 (e.g., M3), an LV electrode 136 (e.g., M2), and an LV electrode 138 (e.g., D1). The RV lead 110 is transvenously inserted into the heart 111 to place the RV coil 122 in the RV apex, and the SVC coil electrode 116. Accordingly, the RV lead 110 is capable of receiving cardiac signals and delivering stimulation in the form of pacing and shock therapy to the right ventricle 140 (also referred to as the RV chamber). The IMD 100 includes RV tip electrode 126, and a right atrium (RA) electrode 123. The RV lead 110 includes an RV tip electrode 126, an RV ring electrode 124, an RV coil electrode 122, and an SVC coil electrode 116.

The IMD 100 includes a left ventricle 142 (e.g., left chamber) pacing therapy, and is coupled to a multi-pole LV lead 114 designed for placement in various locations such as a "CS region" (e.g., venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus), the epicardial space, and/or the like.

In an embodiment, the LV lead 114 is designed to receive atrial and ventricular cardiac signals and to deliver left ventricular pacing therapy using a set of multiple LV electrodes 132, 134, 136, 138. The LV lead 114 also may deliver left atrial pacing therapy using at least an LA ring electrode 128 and shocking therapy using at least the LA ring electrode 128. In alternate embodiments, the LV lead 114 includes the LV electrodes 138, 136, 134, and 132, but does not include the LA electrode 130. The LV lead 114 may be, for example, the Quartet™ LV pacing lead developed by St. Jude Medical Inc. (headquartered in St. Paul, Minn.), which includes four pacing electrodes on the LV lead. Although three leads 110, 112, and 114 are shown in FIG. 1, fewer or additional leads with various configurations of pacing, sensing, and/or shocking electrodes may optionally be used. For example, the LV lead 114 may have more or less than four LV electrodes 132-138.

The LV electrode 132 (also referred to as P4) is shown as being the most "distal" LV electrode with reference to how far the electrode is from the right ventricle 140. The LV electrode 138 (also referred to as D1) is shown as being the most "proximal" LV electrode 132-138 to the left ventricle 142. The LV electrodes 136 and 134 are shown as being "middle" LV electrodes (also referred to as M3 and M2), between the distal and proximal LV electrodes 138 and 132, respectively. Accordingly, so as to more aptly describe their relative locations, the LV electrodes 138, 136, 134, and 132 may be referred to respectively as electrodes D1, M2, M3, and P4 (where "D" stands for "distal", "M" stands for "middle", and "P" stands from "proximal", and the s are arranged from most distal to most proximal, as shown in FIG. 1). Optionally, more or fewer LV electrodes may be provided on the lead 114 than the four LV electrodes D1, M2, M3, and P4.

The LV electrodes 132-138 are configured such that each electrode may be utilized to deliver pacing pulses and/or sense pacing pulses (e.g., monitor the response of the LV tissue to a pacing pulse). In a pacing vector or a sensing vector, each LV electrode 132-138 may be controlled to function as a cathode (negative electrode). Pacing pulses may be directionally provided between electrodes to define a pacing vector. In a pacing vector, a generated pulse is applied to the surrounding myocardial tissue through the cathode. The electrodes that define the pacing vectors may be electrodes in the heart 111 or located externally to the heart 111 (e.g., on a housing/case device 101). For example, the housing/case 101 may be referred to as the housing 101 and function as an anode in unipolar pacing and/or sensing vectors. The RV coil 122 may also function as an anode in unipolar pacing and/or sensing vectors. The LV electrodes 132-138 may be used to provide various different vectors. Some of the vectors are intraventricular LV vectors (e.g., vectors between two of the LV electrodes 132-138), while other vectors are interventricular (e.g., vectors between an LV electrode 132-138 and the RV coil 122 or another electrode remote from the left ventricle 142). Various exemplary bipolar sensing vectors with LV cathodes that may be used for sensing using the LV electrodes D1, M2, M3, and P4 and the RV coil 122. Various other types of leads and the IMD 100 may be used with various other types of electrodes and combinations of electrodes. Utilizing an RV coil electrode as an anode is merely one example. Various other electrodes may be configured as the anode electrode.

Figure 2:
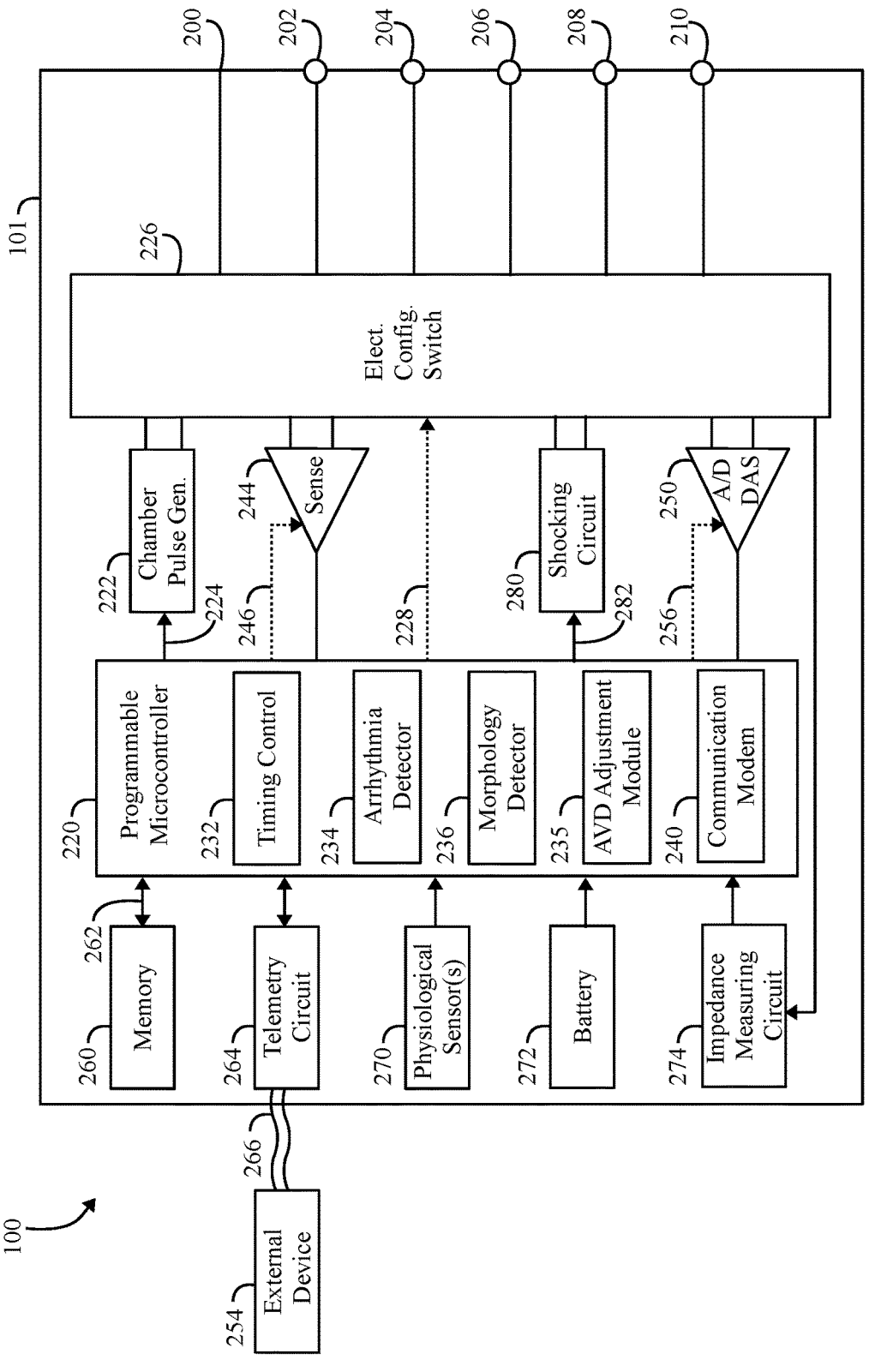
FIG. 2 illustrates a schematic view of the IMD in accordance with embodiments herein.

FIG. 2 illustrates a schematic view of the IMD 100. The IMD 100 may be a dual-chamber stimulation device, capable of treating both fast and slow arrhythmias with stimulation therapy, including cardioversion, pacing stimulation, an implantable cardioverter defibrillator, suspend tachycardia detection, tachyarrhythmia therapy, and/or the like.

The IMD 100 has a housing 101 to hold the electronic/computing components. The housing 101 (which is often referred to as the "can," "case," "encasing," or new to me makes "case electrode") may be programmably selected to act as the return electrode for certain stimulus modes. The housing 101 further includes a connector (not shown) with a plurality of terminals 200-210. The terminals may be connected to electrodes that are located in various locations within and around the heart. For example, the terminals may include: a terminal 200 to be coupled to a first electrode (e.g., a tip electrode) located in a first chamber; a terminal 202 to be coupled to a second electrode located in a second chamber; a terminal 204 to be coupled to an electrode located in the first chamber; a terminal 206 to be coupled to an electrode located in the second chamber; an a terminal 208 to be coupled to an electrode; and a terminal 210 to be coupled to an electrode located in the shocking circuit 280. The type and location of each electrode may vary. For example, the electrodes may include various combinations of a ring, a tip, a coil and shocking electrodes and the like.

The IMD 100 includes a programmable microcontroller 220 that controls various operations of the IMD 100, including cardiac monitoring and stimulation therapy. The microcontroller 220 includes a microprocessor (or equivalent control circuitry), one or more processors, RAM and/or ROM memory, logic and timing circuitry, state machine circuitry, and I/O circuitry. The IMD 100 further includes an atrial and/or ventricular pulse generator 222 that generates stimulation pulses for connecting the desired electrodes to the appropriate I/O circuits, thereby facilitating electrode programmability. The switch 226 is controlled by a control signal 228 from the microcontroller 220.

A pulse generator 222 is illustrated in FIG. 2. Optionally, the IMD 100 may include multiple pulse generators, similar to the pulse generator 222, where each pulse generator is coupled to one or more electrodes and controlled by the microcontroller 220 to deliver select stimulus pulse(s) to the corresponding one or more electrodes. The IMD 100 includes sensing circuits 244 selectively coupled to one or more electrodes that perform sensing operations, through the switch 226 to detect the presence of cardiac activity in the chamber of the heart 111. The output of the sensing circuits 244 is connected to the microcontroller 220 which, in turn, triggers, or inhibits the pulse generator 222 in response to the absence or presence of cardiac activity. The sensing circuits 244 receives a control signal 246 from the microcontroller 220 for purposes of controlling the gain, threshold, polarization charge removal circuitry (not shown), and the timing of any blocking circuitry (not shown) coupled to the inputs of the sensing circuits.

In the example of FIG. 2, the sensing circuit 244 is illustrated. Optionally, the IMD 100 may include multiple sensing circuits 244, similar to the sensing circuit 244, where each sensing circuit is coupled to one or more electrodes and controlled by the microcontroller 220 to sense electrical activity detected at the corresponding one or more electrodes. The sensing circuit 224 may operate in a unipolar sensing configuration or a bipolar sensing configuration.

The IMD 100 further includes an analog-to-digital (A/D) data acquisition system (DAS) 250 coupled to one or more electrodes via the switch 226 to sample cardiac signals across any pair of desired electrodes. The DAS 250 is configured to acquire intracardiac electrogram signals, convert the raw analog data into digital data and store the digital data for later processing and/or telemetric transmission to an external device 254 (e.g., a programmer, local transceiver, or a diagnostic system analyzer). The DAS 250 is controlled by a control signal 256 from the microcontroller 220.

The microcontroller 220 includes an arrhythmia detector 234 for analyzing cardiac activity signals sensed by the sensing circuit 244 and/or the DAS 250. The arrhythmia detector 234 is configured to analyze cardiac signals sensed at various sensing sites.

The microcontroller 220 further includes an AVD adjustment module 235 that is configured to perform, among other things, the operations of the methods described herein. The AVD adjustment module 235 detects an atrial paced (Ap) event or atrial sensed (As) event; determines a measured AV interval corresponding to an interval between the Ap event or the As event and a ventricular sensed event; calculates a percentage-based (PB) offset based on the measured AV interval; and automatically dynamically adjusts an AV delay, utilized by the IMD, based on the measured AV interval and the PB offset. The AVD adjustment module 235 manages a pacing therapy, utilized by the IMD, based on the AV delay after the adjusting operation.

The AVD adjustment module 235 is further configured to set the PB offset to equal a programmed percentage of the measured AV interval, and set the AV delay to correspond to a difference between the measured AV interval and the PB offset. The AVD adjustment module 235 is further configured to perform the calculating and adjusting operations by setting the AV delay, in connection with the As event, as AVDs=[(As-Vs interval)−(PB offset)], wherein the PB offset=(As-Vs interval)*P1%], the As-Vs interval corresponds to the measured AV interval between the As event and a sensed ventricular (Vs) event, and the P1% corresponds to a pre-programmed percentage.

In connection with some embodiments, an electrode is provided proximate to a left ventricular (LV) site. The AVD adjustment module 235 is further configured to determine the measured AV interval by determining a measured A-RV interval and a measured A-LV interval. The AVD adjustment module 235 is further to adjust the AV delay by adjusting, as the AV delay: a delay associated with the As event to a right sensed ventricular (RVs) event as A-RVDs=[(As-RVs interval)−(PBs-RV offset)], wherein the PBs-RV offset represents a first percentage based offset between the As event and the RVs event; and a delay associated with the As event to a left ventricular sensed (LVs) event as A-RVDs=[(As-LVs interval)−(PBs-LV offset)], wherein PBs-LV offset represents a second percentage based offset between the As event and the LVs event. The AVD adjustment module 235 is further configured to log a base heart rate associated with the measured AV interval. The AVD adjustment module 235 is further configured to monitor a current heart rate, and automatically repeat the determining, calculating and adjusting operations when the current heart rate changes by more than a predetermined threshold relative to the base heart rate. The AVD adjustment module 235 is further configured to extend the AV delay in proportion to a ratio between the current heart rate and the base heart rate when the current heart rate is slower than the base heart rate.

The AVD adjustment module 235 is further configured to: extend the AV delay to correspond to a default search AV delay (AVD$_{search}$); sensing cardiac activity for a predetermined number of cardiac beats; identify whether the cardiac activity is indicative of a conduction block condition or non-conduction block condition; and repeat the determining, calculating and adjusting operations only when the non-conduction block condition is identified. The AVD adjustment module 235 is further configured to perform the identifying operation by identifying the cardiac activity to be indicative of a conduction block condition when fewer than a select number of cardiac beats exhibit sensed ventricular events during the default search AV delay AVD$_{search}$. The AVD adjustment module 235 is further configured to adjust a sensed AV delay (AVDs) and a paced AV delay (AVDp), identify a presence of conduction block and, in response thereto, revert the AVDs and base AVDp to AVDs-base and AVDp-base programmed lengths, respectively; and maintain the base AVDp-base and AVDs-base programmed lengths for a select second number of cardiac beats.

The microcontroller 220 is operably coupled to a memory 260 by a suitable data/address bus 262. The programmable operating parameters used by the microcontroller 220 are stored in the memory 260 and used to customize the operation of the IMD 100 to suit the needs of a particular patient. The operating parameters of the IMD 100 may be non-invasively programmed into the memory 260 through a telemetry circuit 264 in telemetric communication via communication link 266 (e.g., MICS, Bluetooth low energy, and/or the like) with the external device 254.

The IMD 100 can further include one or more physiological sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. While shown as being included within the IMD 100, the physiological sensor(s) 270 may be external to the IMD 100, yet still, be implanted within or carried by the patient. Examples of physiological sensors might include sensors that, for example, sense respiration rate, pH of blood, ventricular gradient, activity, position/posture, minute ventilation (MV), and/or the like.

A battery 272 provides operating power to all of the components in the IMD 100. The battery 272 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the IMD 100 employs lithium/silver vanadium oxide batteries.

The IMD 100 further includes an impedance measuring circuit 274, which can be used for many things, including sensing respiration phase. The impedance measuring circuit 274 is coupled to the switch 226 so that any desired electrode and/or terminal may be used to measure impedance in connection with monitoring respiration phase.

The microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 11 to 40 joules), as controlled by the microcontroller 220. Such shocking pulses are applied to the patient's heart through shocking electrodes. Maybe noted that the shock therapy circuitry is optional and may not be implemented in the IMD 100.

The microcontroller 220 further includes timing control 232 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. The switch 226 includes a plurality of switches for connecting the desired electrodes to the appropriate I/O circuits, thereby providing complete electrode programmability. Accordingly, the switch 226, in response to a control signal 228 from the microcontroller 220, determines the polarity of the stimulation pulses (e.g., unipolar, bipolar, etc.) by selectively closing the appropriate combination of switches (not shown) as is known in the art.

The microcontroller 220 is illustrated to include timing control 232 to control the timing of the stimulation pulses (e.g., pacing rate, atrioventricular (AV) delay, atrial interconduction (A-A) delay, or ventricular interconduction (V-V) delay, etc.). The AV delay is managed to provide a fusion AV delay to fuse timing of pacing pulses with intrinsic wave fronts. The timing control 232 may also be used for the timing of refractory periods, blanking intervals, noise detection windows, evoked response windows, alert intervals, marker channel timing, and so on. Microcontroller 220 also has a morphology detector 236 to review and analyze one or more features of the morphology of cardiac signals. Although not shown, the microcontroller 220 may further include other dedicated circuitry and/or firmware/software components that assist in monitoring various conditions of the patient's heart and managing pacing therapies.

The IMD 100 is further equipped with a communication modem (modulator/demodulator) 240 to enable wireless communication with other devices, implanted devices and/or external devices. In one implementation, the communication modem 240 may use high-frequency modulation of a signal transmitted between a pair of electrodes. As one example, the signals may be transmitted in a high-frequency range of approximately 10-80 kHz, as such signals travel through the body tissue and fluids without stimulating the heart or being felt by the patient.

Figure 3:
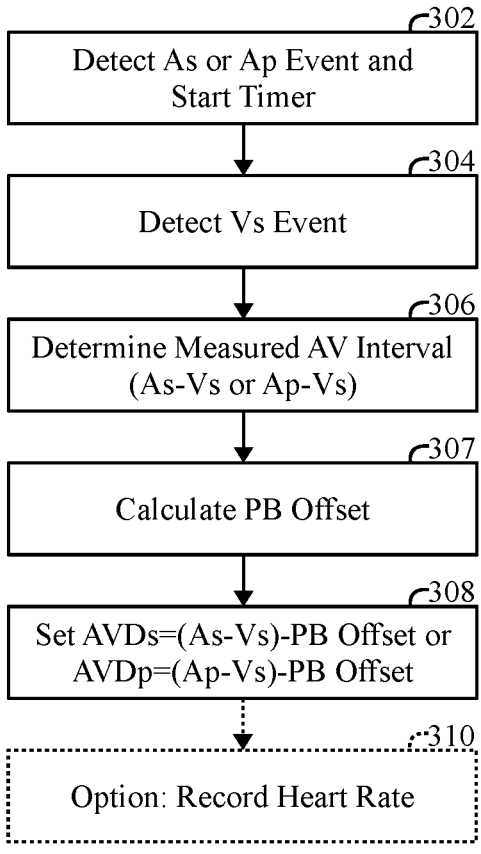
FIG. 3 illustrates a computer implemented method for dynamic device-based AV delay adjustment in accordance with embodiments herein.

FIG. 3 illustrates a computer implemented method for dynamic device-based AV delay adjustment in accordance with embodiments herein. The method is under control of one or more processors configured with specific executable instructions. As explained hereafter, the operations of FIG. 3 may be performed during a search mode in connection with a desired one or more cardiac beats measured during the search mode. Optionally, the operations of FIG. 3 may be performed following termination of the search mode after an identification of whether a patient is experiencing normal conduction or an abnormal conduction block condition.

Optionally, the operations of FIG. 3 may be performed when the heart rate changes, relative to a base heart rate, by more than a threshold level.

At 302, the one or more processors detect a paced atrial (Ap) event or sensed atrial (As) event. When the paced or sensed atrial event is detected, one or more AV timers are started.

At 304, the one or more processors monitor for a sensed ventricular (Vs) event. The Vs event may occur at an RV sensing site or an LV sensing site. Optionally, an RV sensed (RVs) event may be detected separate from a sensed LV (LVs)(LBS) event that is detected.

At 306, the one or more processors determine a measured AV interval. The measured AV interval may correspond to an interval between a sensed atrial event and a sensed ventricular event (As-Vs interval) and/or an interval between a paced atrial event and a sensed ventricular event (Ap-Vs interval).

At 307, the one or more processors calculate a percentage based (PB) offset that is derived from the measured AV interval. For example, the PB offset may be set to equal a percentage (e.g., 20%) of the measured AV interval, such as PB offset=(AV interval)*P1%, where P1% corresponds to a percentage that is programmed by a clinician and/or automatically derived by the IMD based on recorded physiologic characteristics. Additionally or alternatively, when separate As-Vs and Ap-Vs intervals are measured, the PB offset may be based solely on the As-Vs interval (e.g., PB offset=(AV interval)*P1%). Additionally or alternatively, an atrial sense related PB offset and atrial pace related PB offset may be calculated based on the As-Vs and/or Ap-Vs intervals, respectively. For example, an atrial pace related PB offset may be calculated as a programmed percentage (e.g., 25%) of the Ap-Vs interval, while an atrial sense related PB offset may be calculated as a program percentage (e.g., 20%) of the As-Vs interval. As a further example, the atrial sense related PB offset may be set as: PBs offset=(As-Vs interval)*P1%, where P1% corresponds to a percentage that is programmed by a clinician and/or automatically derived by the IMD based on recorded physiologic characteristics. The atrial pace related PB offset may be set as: PBp offset=(Ap-Vs interval)*P2%, where P2% corresponds to a percentage that is programmed by a clinician and/or automatically derived by the IMD based on recorded physiologic characteristics.

At 308, the one or more processors automatically and dynamically adjust one or more AV delays based on the measured AV interval and the PB offset(s). For example, the one or more processors may set an AV delay associated with sensed atrial events as AVDs=[(As-Vs interval)−(PBs offset)], where the PBs offset is calculated based on the percentage P1% of the As-Vs interval. As another example, the one or more processors may set an AV delay associated with a paced atrial event as AVDp=[(Ap-Vs interval)−(PBp offset)], where the PBp offset is calculated based on the percentage (P2%) of the Ap-Vs interval.

Additionally or alternatively, each time the methods and systems herein reset/reprogram the AVDs and AVDp values, the current heart rate is logged rate. Accordingly, an optional operation may be provided at 310, in which the one or more processors record the current heart rate as a "base" or "logged" heart rate corresponding to the measured AV interval that is utilized to set the AVDs and AVDp values. As explained below in connection with FIG. 6, an automatic rate-responsive AVDs and AVDp adjustment may be performed when the heart rate reduces. As that heart rate slows down, the AVDs and AVDp values are automatically extended, such as in a linear fashion, until the next time that the AV interval is measured (e.g., up to 256 beats later).

The IMD manages a pacing therapy utilizing various AV delays that are changed over the course of operation based on various criteria, such as particular physiologic behavior exhibited by the heart, completion of predetermined numbers of cardiac beats, and the like.

Figure 4:
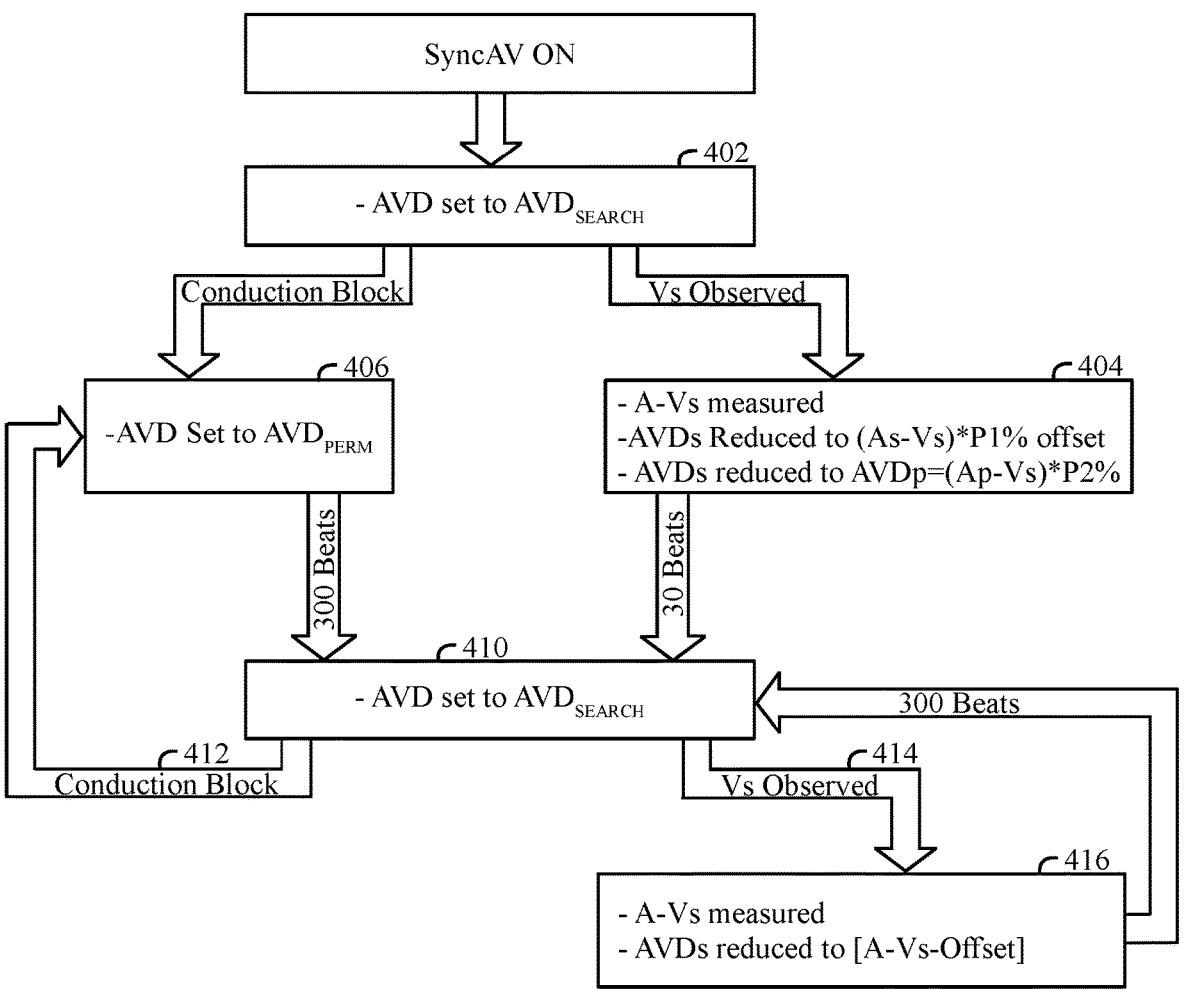
FIG. 4 illustrates an overall process for implementing the AV synchronization in accordance with embodiments herein.

FIG. 4 illustrates an overall process for implementing the AV synchronization in accordance with embodiments herein. The AV synchronization process utilizes the dynamic device-based AV delay adjustment process of FIG. 3 (and/or FIG. 5).

At 402, when the AV synchronization process is activated, the one or more processors enter a search mode, in which the processors set the AVDp and AVDs values to equal corresponding AV search delays (collectively referred to as AVD$_{search}$). The AV search delays are set to be sufficiently long to wait for an intrinsic RV event that may be delayed following a paced atrial or sensed atrial event. However, the AV search delays, AVD$_{search}$, are not too long in order to avoid delaying pacing when a patient should otherwise be paced. For example, the AVD$_{search}$ may be set to between 300 and 400 ms, and more preferably the AVDp may be set to equal 300 ms to 350 ms, while the AVDs may be set to equal 325 ms to 375 ms. Additionally or alternatively, one AVD$_{search}$ may be set in connection with measuring an As-Vs interval (e.g., 325 ms), while a second AVD$_{search}$ may be set in connection with measuring an Ap-Vs interval (e.g., 350 ms). The processors may remain in the search mode for a predetermined number of beats (e.g., 5 beats, 10 beats) and/or a predetermined period of time (e.g., 10 second). Additionally or alternatively, the processors may remain in the search mode until a condition is satisfied, such as detecting a particular physiologic pattern (e.g., detecting 3 consecutive Vs events). While in the search more, the processors track the cardiac activity.

When the search mode is terminated, the one or more processors determine whether the tracked cardiac activity is indicative of conduction block or whether a sufficient number of Vs events were detected. For example, when all or a select number of the beats, during the search mode, exhibit Vs events that are detected before the AVD$_{search}$ time expires, the processors may declare the series of beats to exhibit a normal or non-blocked condition, in response to which flow moves to 404. As a further example, during a series of 4-8 beats, 3 or more consecutive beats may exhibit sensed ventricular Vs events before the AVD$_{search}$ time expires, in which case the processors declare the series of events to be normal.

When flow advances to 404, the one or more processors measure one or more AV intervals and set the AVD based on the measured AV interval as described herein (e.g., in connection with the operations of FIGS. 3 and/or 5). The As-Vs interval and Ap-Vs interval used to define the AVDs and AVDp values may be determined from a select end or intermediate one of the beats measured during the search mode, such as the third or fourth event/beat in order to allow for the AV interval to stabilize following the change to the $AVD_{search}$ time. Optionally, the As-Vs interval and Ap-Vs interval may be calculated as an average (or other mathematical combination) of multiple As-Vs intervals and Ap-Vs intervals, respectively, for a desired number of multiple beats. Optionally, the AVDs and AVDp may be set at 404 in various manners, based upon the nature of the events that occur during the search mode. For example, both of the AVDs and AVDp values may be set, as noted above in connection with FIG. 3, in response to a select number (e.g., three-five) consecutive Vs events occurring during the search mode (at 402).

Additionally or alternatively, the AVDs and AVDp delays may be set in alternative manners in response to other combinations of atrial and ventricular events occurring during the search mode. It may be desirable to utilize select combinations of atrial and ventricular events as a criteria for setting the AVDs and AVDp delays, such as in order to skip single or paired ectopic premature ventricular contractions (PVCs). For example, the one or more processors may search for a particular type of atrial event during a select beat within the search mode. For example, the one or more processors may determine the type of atrial event that occurs during the third, fourth or fifth beat during the search mode, and based thereon, set the AVDs and AVDp delays in a desired manner. As a more specific example, when the processors determine that a sensed atrial As event occurs during the third beat, but before the third sensed ventricular event, the processors may set the AV delays as follows: AVDs=(As-Vs interval)−(PBs offset) and AVDp=(As-Vs interval)−PBs offset)*R, where R may be a ratio between the measured Ap-Vs interval and As-Vs interval (e.g., R=(Ap-Vs)/(As-Vs)). In the foregoing example, both of the AVDs and AVDp are set based on the As-Vs interval and PBs offset. When either of the Ap-Vs interval or As-Vs interval cannot be measured, the value for R may be a preprogrammed ratio (e.g., 1.3-1.5). As another specific example, alternatively, when the processors determine that a paced atrial Ap event occurs before the third sensed ventricular event, the processors may set the AV delays based on the Ap-Vs interval and PBp offset as follows: AVDp=(Ap-Vs interval)−(PBp offset) and AVDp=(Ap-Vs interval)−(PBp offset)/R. By setting the AVDs and AVDp based on the type of atrial event that occurred during the third or a later beat, the processors skip single or paired ectopic PVC beats.

The AVDp and AVDs values set at 404 are maintained for a select first number of cardiac beats (e.g., 20-40 beats) associated with a normal or non-conduction block condition.

Returning to 402, when fewer than the select number of the beats exhibit Vs events during the $AVD_{search}$, the processors may declare the series of beats to exhibit an abnormal or conduction block condition. When an abnormal or conduction block condition is identified, flow moves to 406. For example, during the search mode, three consecutive Vs events do not occur. Alternatively, during the series of 4-8 beats, fewer than 3 consecutive beats may exhibit Vs events before the $AVD_{search}$ time expires.

At 406, the processors identify the presence of conduction block (or a similar abnormal condition), and in response thereto, revert the AVDs and AVDp delays to base programmed lengths (e.g., set $AVDp_{-base}$ equal to 100 ms to 150 ms and set $AVD_{s-base}$ equal to 125 ms to 175 ms). The base AVDp-base and $AVD_{s-base}$ lengths are maintained for a select second number of cardiac beats (e.g., 200-300 beats).

The AVDp and AVDs values set at 404 or 406 are utilized by the IMD for corresponding numbers of cardiac beats (e.g., 20-40 or 200-300), and thereafter flow continues to 410. At 410, after the corresponding number of select cardiac beats, the one or more processors reset the AVDp and AVDs values to the AV search delay $AVD_{search}$, thereby reentering a search mode. The AV search delays set at 410 may be the same as or differ from the AV search delays set at 402. The duration of the search mode at 410 may be the same as or different from the duration of the search mode at 402. For example, the processors may maintain the search mode at 410 for 5 or more beats with the AVDp=350 ms and AVDs=325 ms. At 410, the one or more processors determine whether a select number of consecutive sensed ventricular Vs events occur and based thereon, flow branches along 412 or 414. For example, when three or another number of consecutive Va events are detected during the search mode, flow branches along 414.

At 414, the one or more processors measure one or more AV intervals and set the AVDp and AVDs based on the measured AV intervals and PB offsets. As explained above in connection with 404, at 416, the As-Vs interval and Ap-Vs interval, used to define the AVDs and AVDp values, may be determined from a select one of the beats measured during the search mode or calculated as an average (or other mathematical combination) of multiple As-Vs intervals and Ap-Vs intervals.

Optionally, the AVDs and AVDp may be set at 416 in other manners, based upon the nature of the events that occurred during the search mode (as described above in connection with 404). For example, when the processors determine that a sensed atrial As event occurs during the third beat, but before the third sensed ventricular event, the processors may set the AV delays as follows: AVDs=[(As-Vs interval)−(As-Vs interval)*P1%] and AVDp=[(As-Vs interval)−(As-Vs interval)*P1%*R]. Alternatively, when the processors determine that a paced atrial Ap event occurs before the third sensed ventricular event, the processors may set the AV delays as follows: AVDs=[(Ap-Vs interval)−(Ap-Vs interval)*P3%] and AVDp=[(Ap-Vs interval)−(Ap-Vs interval)*P3%/R]. Thereafter, the AVDp and AVDs values set at 416 are maintained for a select number of cardiac beats (e.g., 200-300 beats).

Returning to 410, when the one or more processors determine that fewer than the select number of consecutive sensed ventricular Vs events occur, the processors determined that the patient exhibited a conduction block condition and in response thereto, flow branches along 412 and returns to 406. For example, the processors may identify a conduction block condition when the processors do not detect three or another select number of consecutive sensed ventricular Vs events during the search mode, and flow branches along 412. As noted above, at 406, the AVDp and AVDs values revert to the base programmed lengths for a longer select number of beats, such as $300 \times 2^N$ beats before reentering the search mode again. The variable N equals the number of consecutive searches in which conduction block was identified.

Additionally or alternatively, anytime the select number of consecutive sensed ventricular Vs events occur while the AVDp and AVDs values are already reduced (e.g., within either a 30- or 300-beat window), both AVDp and AVDs values are further reduced, as described above, such as for another 30 beats before re-entering the search mode. Additionally or alternatively, whenever the processors determine that it is desirable to further reduce the AVDp and AVDs values, after already being reduced, the processors may first enter the search mode for a shortened search window (e.g., after 30 beats instead of 300 beats) to allow the processors to perform a fast AV interval assessment.

The foregoing process of FIG. 3 for dynamically adjusting paced and sensed AV delays is described in connection with one example of an overall synchronization process (FIG. 4). Optionally, the dynamic process of FIG. 3 may be implemented in connection with other static or dynamic methods for programming paced and sensed AV delays.

FIG. 5 illustrates a process for dynamically adjusting paced and sensed AV delays in accordance with an alternative embodiment. In the example of FIG. 5, the process of FIG. 3 for utilizing a percentage based offset is expanded to apply independently to an RV pacing site and one or more LV pacing sites, such as when RV and LV leads are separately implanted. As explained hereafter, a first AVDs and first AVDp are calculated in connection with an RV sensing/pacing site, and a second AVDs and second AVDp are calculated in connection with an LV sensing/pacing site. The operations of FIG. 5 may be performed during one or more of the search modes (described in connection with FIG. 4) in connection with a desired one or more cardiac beats measured during the search mode. Optionally, the operations of FIG. 5 may be performed following termination of the search mode after an identification of whether a patient is experiencing normal conduction or an abnormal conduction block condition.

At 502, the one or more processors detect a paced atrial Ap event or sensed atrial As event. When the paced or sensed atrial event is detected, an A-LV timer is started and an A-RV timer is started.

At 504, the one or more processors monitor for and detect a right sensed ventricular RVs event, and monitor for and detect a left sensed ventricular LVs event. The RVs event occurs at an RV sensing site and the LVs event occurs at an LV sensing site. When the LV lead includes multiple electrodes, such as in connection with multipoint pacing (MPP), various ones of the LV electrodes may be designated to be utilized as the LV sensing site. By way of example, the distal or one of the intermediate LV sensing sites may be utilized to monitor for and detect left sensed ventricular events.

At 506, the one or more processors determine a measured A-RV interval and a measured A-LV interval. The measured A-RV interval may correspond to an interval between a sensed atrial event and a sensed right ventricular event (As-RVs interval) and/or an interval between a paced atrial event and a right sensed ventricular event (AP-RVs interval). The measured A-LV interval may correspond to an interval between a sensed atrial event and a sensed left ventricular event (As-LVs interval) and/or an interval between a paced atrial event and a sensed left ventricular event (Ap-LVs interval).

At 507, the one or more processors calculate a percentage based (PB) offset based on the measured AV interval. For example, the PB offset may be set to equal a programmed percentage (e.g., 20%) of the measured AV interval, such as PB offset=(AV interval)*P1%, where P1% corresponds to a percentage that is programmed by a clinician and/or automatically derived by the IMD based on recorded physiologic characteristics. Additionally or alternatively, when separate As-Vs and Ap-Vs intervals are measured, the PB offset may be based solely on the As-Vs interval (e.g., PB offset=(As-Vs interval)*P1%).

Additionally or alternatively, as explained above in connection with FIG. 3, an atrial sense related PB offset and atrial pace related PB offset may be calculated separately on the As-Vs and/or Ap-Vs intervals, respectively. Further, separate PB offsets may be calculated in connection with the LV sensing/pacing site(s). For example, an atrial pacerelated PB offset may be calculated as a programmed percentage (e.g., 25%) of the Ap-LVs interval, while an atrial sense related PB offset may be calculated as a program percentage (e.g., 20%) of the As-LVs interval. As a further example, separate PB offsets may be calculated in connection with each sensed atrial and paced atrial event relative to each RV sensing/pacing site and relative to each LV sensing/pacing site (e.g., PBs-RV offset, PBp-RV offset, PBs-LV offset, PBp-LV offset). The programmed percentage that is used to calculate the offsets associated with the RV may differ from the programmed percentage that is used to calculate the offsets associated with the LV.

At 508, the one or more processors automatically and dynamically adjusts one or more A-RV delays and one or more A-LV delays. For example, the one or more processors may set a delay associated with a sensed atrial event to sensed right ventricular event as A-RVDs=[(As-RVs interval)−(PBs-RV offset)]. As another example, the one or more processors may set a delay associated with a paced atrial event to sensed right ventricular event as A-RVDp=[(Ap-RVs interval)−(PBp-RV offset). Similarly, the one or more processors set the delays associated with sensed atrial/paced events to sensed left ventricular events as A-LVDs=[(As-LVs interval)−(PBs-LV offset)] and A-LVDp=[(As-LVp interval)−(PBp-RV offset)].

An optional operation may be provided at 510, in which the one or more processors record the current heart rate as a "base" or "logged" heart rate corresponding to the measured AV interval that is utilized to set the AVDs and AVDp values. As explained below in connection with FIG. 6, an automatic rate-responsive AVDs and AVDp adjustment may be performed when the heart rate changes.

The operations of FIG. 5 are described in connection with a single RV pacing/sensing site and a single LV pacing/sensing site. Optionally, the proposed independent A-RV and A-LV delays, may be expanded for use with multiple LV pacing/sensing sites. With biventricular MPP, AVDs and AVDp values for three or more pacing sites may be dynamically programmed: A-RVDs and A-RVDp, A-LVDs1 and A-LVDp1, and A-LVDs2 and A-LVDp2. Optionally, with LV-only MPP, only two AVD values would be dynamically programmed: A-LVDs1 and A-LVDp1, and A-LVDs2 and A-LVDp2 such as for an intermediate and distal electrodes.

FIG. 6 illustrates a process for automatically adjusting sensed and paced AV delays, in connection with changes in heart rate, in accordance with embodiments herein. At 602, the one or more processors monitor the heart rate. At 604, the one or more processors compare the current heart rate to a base heart rate that was logged when setting the paced and sensed AV delays as described herein (e.g., as set at 308 in FIG. 3, at 404 or 410 in FIG. 4, or at 508 in FIG. 5). The processors determine whether any change has occurred between the current heart rate and the base heart rate. When a change occurs, the processors determine whether the change in the heart rate exceeds a threshold. For example, one or more thresholds may be defined, such that small changes in heart rate do not warrant adjustment of the sensed and/or paced AV delays. When the change in heart rate does not exceed the threshold, flow returns to 602. Alternatively, when the change in heart rate exceeds the threshold, the processors interpret this condition to indicate that the heart rate has sufficiently changed to indicate that the intrinsic AV interval has similarly changed and thus warrant a change in the programmed sensed and paced AV delays. Accordingly, flow advances from 604 to 606.

At 606, the one or more processors determine a relationship between the current heart rate and the base heart rate. For example, the ratio may indicate a percentage increase or decrease in the current heart rate over the base heart rate. Optionally, the processors may determine the relationship in a manner other than a ratio. For example, the relationship may be defined as a difference between the current and base heart rates, an average (or other mathematical combination) of the current and base heart rates, and the like.

At 608, the one or more processors adjust lengths of the AVDs and AVDp based on the relation between the current and base heart rates. For example, when the ratio of the current and base heart rates indicate that the current heart rate is slower than the heart rate that was logged when setting the prior AVDs and AVDp, the processors automatically extend the AVDs and AVDp in proportion to the ratio of the current and base heart rates. For example, when the current heart rate falls below a base heart rate by 10%, the AVDs and AVDp may be extended similarly by 10%. Alternatively, when the current heart rate increases to be faster than the logged heart rate, the processors may automatically shorten the AVDs and AVDp in proportion to the ratio of the current and base heart rates.

The embodiment of FIG. 6 enables dynamic adjustment of the AVDs and AVDp to automatically follow changes in the intrinsic AV interval that inherently follow changes in heart rate (e.g., activity, relaxation). The embodiment of FIG. 6 avoids an undue delay, when the heart rate drops (and AV interval lengthens), that may otherwise result (e.g., up to 3-5 min) in systems and methods that only check for longer AV intervals after an extended number of cardiac beats (e.g., every 256 beats). Instead, the embodiment of FIG. 6 provides an automatic rate-responsive AVDs and AVDp adjustment when the heart rate reduces. Each time methods and systems herein reset/reprogram the AVDs and AVDp values, the current heart rate is logged as the new base heart rate. As that heart rate slows down, the AVDs and AVDp values are automatically extended in a linear fashion, until the next time re-measurement of the AV interval (e.g., up to 256 beats later).

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A method for dynamic device-based atrio-ventricular (AV) delay adjustment, the method comprising:

utilizing one or more processors, in an implantable medical device (IMD), for:

A) extending the AV delay to a default search AV delay ($AVD_{search}$);

B) sensing cardiac activity for a predetermined number of cardiac beats;

C) when the cardiac activity is indicative of a non-conduction block condition, performing following:

C1) determining an AV interval corresponding to an interval between an atrial paced (Ap) event or an atrial sensed (As) event and a ventricular sensed event;

C2) calculating a percentage-based (PB) offset based on the AV interval;

C3) adjusting an AV delay based on the AV interval and the PB offset; and

D) managing a pacing therapy, utilized by the IMD, based on the AV delay.

2. The method of claim 1, further comprising:

determining that the cardiac activity for a first number of cardiac beats is indicative of a non-conduction block condition, and in response thereto, performing the operations at C1) to C3); and determining that the cardiac activity for a second number of cardiac beats is indicative of a conduction block condition, and in response thereto, not performing the operations at C1) to C3).

3. The method of claim 2, further comprising, in response to determining that the cardiac activity is indicative of a conduction block condition, setting the AV delay to a base programmed AV delay.

4. The method of claim 2, wherein the calculating operation further comprises setting the PB offset to equal a programmed percentage of the AV interval, and wherein the adjusting operation further comprises setting the AV delay to correspond to a difference between the AV interval and the PB offset.

5. The method of claim 1, wherein the adjusting is performed automatically and dynamically.

6. The method of claim 1, further comprising providing electrodes configured to be located proximate to an atrial (A) site and a right ventricular (RV) site; and detecting the Ap event or As event.

7. The method of claim 1, further comprising providing an electrode configured to be proximate to a left ventricular (LV) site, wherein the AV interval comprises a measured A-RV interval and a measured A-LV interval, the adjusting operation further comprising adjusting, as the AV delay:

a delay associated with the As event to a right sensed ventricular (RVs) event as A-RVDs=[(As-RVs interval)−(PBs-RV offset)], wherein the PBs-RV offset represents a first percentage based offset between the As event and the RVs event; and a delay associated with the As event to a left ventricular sensed (LVs) event as A-RVDs=[(As-LVs interval)−(PBs-LV offset)], wherein PBs-LV offset represents a second percentage based offset between the As event and the LVs event.

8. The method of claim 1, further comprising monitoring a current heart rate, and automatically repeating the C1) determining, C2) calculating and C3) adjusting operations when the current heart rate changes by more than a predetermined threshold relative to the base heart rate.

9. The method of claim 8, further comprising extending the AV delay in proportion to a ratio between the current heart rate and the base heart rate when the current heart rate is slower than the base heart rate.

10. An implantable medical device (IMD), comprising:

memory to store program instructions;

one or more processors configured to implement the program instructions to:

A) extend the AV delay to correspond to a default search AV delay ($AVD_{search}$);

B) sense cardiac activity for a predetermined number of cardiac beats;

C) when the cardiac activity is indicative of a non-conduction block condition, perform following:

C1) determine an AV interval corresponding to an interval between an atrial paced (Ap) event or an atrial sensed (As) event and a ventricular sensed event;

C2) calculate a percentage-based (PB) offset based on the AV interval;

C3) adjust an AV delay based on the AV interval and the PB offset; and

D) manage a pacing therapy, utilized by the IMD, based on the AV delay.

11. The device of claim 10, wherein the one or more processors are configured to:

determine that the cardiac activity for a first number of cardiac beats is indicative of a non-conduction block condition, and in response thereto, performing the operations at C1) to C3); and determine that the cardiac activity for a second number of cardiac beats is indicative of a conduction block condition, and in response thereto, not performing the operations at C1) to C3).

12. The device of claim 11, wherein, when the cardiac activity is indicative of a conduction block condition, the one or more processors are further configured to set the AV delay to a base programmed AV delay.

13. The device of claim 11, wherein the one or more processors are further configured to set the PB offset to equal a programmed percentage of the AV interval and set the AV delay to correspond to a difference between the AV interval and the PB offset.

14. The device of claim 10, further comprising: electrodes configured to be located proximate to an atrial (A) site and a right ventricular (RV) site, and wherein the one or more processors are configured to detect the Ap event or As event utilizing the electrodes.

15. The device of claim 10, further comprising an electrode configured to be proximate to a left ventricular (LV) site, wherein the AV interval comprises a measured A-RV interval and a measured A-LV interval, the one or more processors to adjust the AV delay by adjusting, as the AV delay:

a delay associated with the As event to a right sensed ventricular (RVs) event as A-RVDs=[(As-RVs interval)−(PBs-RV offset)], wherein the PBs-RV offset represents a first percentage based offset between the As event and the RVs event; and a delay associated with the As event to a left ventricular sensed (LVs) event as A-RVDs=[(As-LVs interval)−(PBs-LV offset)], wherein PBs-LV offset represents a second percentage based offset between the As event and the LVs event.

16. The device of claim 10, further comprising one or more AV timers configured to be started upon detection of the Ap event or As event and stopped upon detection of the ventricular sensed event.

17. The device of claim 16, wherein the one or more processors are configured to monitor a current heart rate, and automatically repeat the determining, calculating and adjusting operations when the current heart rate changes by more than a predetermined threshold relative to the base heart rate.

18. The device of claim 17, wherein the one or more processors are configured to extend the AV delay in proportion to a ratio between the current heart rate and the base heart rate when the current heart rate is slower than the base heart rate.

* * * * *